United States Patent [19]

Khanna et al.

[11] Patent Number: 4,857,455
[45] Date of Patent: Aug. 15, 1989

[54] METHOD FOR THE DETERMINATION OF PEROXIDASE USING FLUOROGENIC SUBSTRATES

[75] Inventors: Pyare L. Khanna, San Jose; Chiu C. Chang, Santa Clara; Edwin F. Ullman, Atherton, all of Calif.

[73] Assignee: Syntex (U.S.A) Inc., Palo Alto, Calif.

[21] Appl. No.: 444,658

[22] Filed: Nov. 26, 1982

[51] Int. Cl.$^4$ .................. G01N 33/535; C12Q 1/26; C12Q 1/28; C12N 9/96

[52] U.S. Cl. ........................... 435/7; 435/25; 435/28; 435/188; 435/810

[58] Field of Search ............... 435/4, 7, 25, 28, 188, 435/805, 810

[56] References Cited

U.S. PATENT DOCUMENTS

| | | | |
|---|---|---|---|
| 4,269,938 | 5/1981 | Frank | 435/28 |
| 4,279,992 | 7/1981 | Boguslaski et al. | 435/810 |
| 4,307,188 | 12/1981 | White | 435/28 |
| 4,318,846 | 3/1982 | Khanna et al. | 435/7 |
| 4,318,981 | 3/1982 | Burd et al. | 435/7 |
| 4,367,238 | 1/1983 | Ueda et al. | 549/269 |
| 4,439,356 | 3/1984 | Khanna et al. | 435/7 |

FOREIGN PATENT DOCUMENTS 60518 9/1982 European Pat. Off. .

OTHER PUBLICATIONS

Weinstein et al, Chemical Abstracts, 92: 22338t, p. 668 (1980).
Barman, *Enzyme Handbook*, vol. I, Springer-Verlag, New York, 234–235 (1969).
Zaitsu et al, Anal. Biochem., 109: 109–113 (1980).
Keston et al, Anal. Biochem., 11: 1–5 (1965).

*Primary Examiner*—Esther M. Kepplinger
*Attorney, Agent, or Firm*—Theodore J. Leitereg; Bertram I. Rowland

[57] ABSTRACT

Novel fluorogenic peroxidase substrates are provided employing novel water soluble activated capped aromatic fluorescent compounds for use as peroxidase substrates. The novel compounds can be used in a wide variety of ways for determination of peroxides, peroxidase, and in assays for analytes employing peroxidase as a label on a member of a specific binding pair.

12 Claims, No Drawings

METHOD FOR THE DETERMINATION OF PEROXIDASE USING FLUOROGENIC SUBSTRATES

BACKGROUND OF THE INVENTION

1. Field of the Invention

Peroxidase is an enzyme which has a large number of desirable properties. It is available, inexpensive, stable to a substantial range of chemical and physical conditions and has a high turnover rate. Besides its obvious use for the determination of peroxidase substrates, it has found ample application in diagnostics for the localization of determinant sites in tissue and the determination in physiological media of a wide variety of analytes. Many analytes are present only in extremely small concentrations and high amplification of the signal is required as a result of a single binding event between the analyte and its homologous binding pair member. Frequently the number of enzyme molecules that signal a binding event is fixed based on the conditions of the assay and improved sensitivity or enhanced signal level is dependent upon a substrate which has a high turnover rate and provides a high signal level.

In developing substrates, there are many constraints. While peroxidase has relatively low specificity, there are limitations on the compounds which can be oxidized. Furthermore, while either the substrate or the product may in principle provide the signal, it is desirable to go from a low signal to a high signal. Therefore, the substrate should contribute little if any detectable signal where the product is measured. Other considerations include the solubility of the substrate and the interaction with materials which may be encountered in the samples to be measured. Additional considerations include ease of synthesis, stability (both shelf-life and in the assay medium), the effect of the production of side products (or even the desired product) on the activity of the peroxidase, and the ability to measure the product providing the detectable signal.

2. Brief Description of the Prior Art

Saunders and Watson, *Biochem. J.* (1950) 46:629–633, describe methoxy-substituted aniline as a peroxidase substrate. Keston and Brandt, *Anal. Biochem.* (1965) 11:1–5, describe fluorogenic substrates and products for use with peroxidase. Zaitsu and Ohkura, Ibid. (1980) 109:109–113 describe a variety of phenolic compounds for use in a fluorimetric assay with peroxidase. A wide variety of phenolic compounds and amines have been reported as chromogenic and fluorogenic substrates for peroxidase.

SUMMARY OF THE INVENTION

Novel substrate fluorogen precursors are provided, employing oxidatively-susceptible-aryl capped fluorescent compounds having ring activating substituents. The compounds are stable under assay conditions in the absence of peroxidase, but in the presence of peroxidase and hydrogen peroxide, the aryl cap is removed in a reaction catalyzed by the peroxidase to provide a stable fluorogenic product. Particularly, umbelliferone and hydroxyxanthene derivatives are joined through a linkage to aryl derivates to provide for a peroxidase substrate which upon oxidation results in removal of the aryl cap where the residual fluorescer has a high fluorescence quantum efficiency.

DESCRIPTION OF THE SPECIFIC EMBODIMENTS

Novel compounds are provided for use as substrates for peroxidase to produce a fluorogenic product in the presence of hydrogen peroxide. The compounds involve an oxidatively-susceptible-aryl cap on a fluorescent compound, which results in the substantial absence of fluorescence in the capped product upon irradiation at the excitation wavelength of the fluorescent product. The substrates are prepared from an amino- or oxy-fluorescent compound, which is preferably relatively stable to peroxidase catalyzed degradation, and an activated carbocyclic aryl group which is bonded to the heteroatom to form a capped substrate for peroxidase. The capped substrate serves as a fluorogenic substrate for peroxidase that is susceptible to catalyzed oxidative removal of the activated aryl group and formation of the fluorescent compound. The substrate may be substituted with a wide variety of groups to enchance water solubility, modify the spectroscopic properties, e.g., excitation and emission wavelength, quantum efficiency, and Stokes shift, or to affect other particular properties of interest, e.g., solubility or photo and enzymic stability of the fluorogenic substrate.

The fluorogenic substrate will usually have at least about 15 carbon atoms, more usually at least about 16 carbon atoms and generally fewer than 60 carbon atoms, more usually fewer than about 50 carbon atoms, having at least 3 heteroatoms and not more than about 18 heteroatoms, usually not more than about 12 heteroatoms, which are selected from nitrogen and chalcogen (oxygen and sulfur), halogen, phosphorus and boron.

There will be at least one activating group bound to an annular carbon atom of the aryl cap, having an atom of atomic number 7–8 (oxy, including hydroxy and ether; and amido and amino, including primary, secondary, and tertiary amino). There will also be a heteroatom (N, O) containing linkage to the aryl cap, so that upon oxidation of the aryl cap, the linkage is cleaved leaving the uncapped fluorescent product.

For the most part, the compounds of the subject invention will have the following formula:

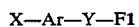     1.

wherein

X is an activating group having oxygen or nitrogen bonded to an annular ring; X is of from 0 to 4, usually 0 to 3 carbon atoms, there being at least one X group and not more than about 3 X groups;

Y is oxy, or carbamyloxy, where the carbamyloxy group $-N(R)CO_2-$ nitrogen is bonded to Fl and R is hydrogen, lower alkyl (1–3 carbon atoms), or a solubilising group bonded to nitrogen through a carbon atom, there usually being two saturated carbon atoms between heteroatoms and the water solubilising group may be bound to lower alkyl; R is usually hydrogen;

Ar is an activated aryl group, normally carbocyclic, particularly phenyl which upon peroxidase catalyzed oxidation serves as a leaving group, generally having from 1 to 2 fused or non-fused rings;

Fl is an aromatic compound, which with the heteroatom (O, N) to which it is attached, provides a fluorescent compound, Fl—OH or F—NHR or salts thereof;

Fl will have at least 9 carbon atoms, more usually at least 10 carbon atoms and not more than about 30 carbon atoms, usually not more than about 26 carbon atoms, and not more than about 16 heteroatoms, more usually not more than about 12 heteroatoms, which include oxygen, nitrogen, sulfur, halogen, boron, and phosphorus. Desirably, there is at least one and not more than about three water solubilizing groups, generally from about one to two water solubilizing groups, normally acidic or basic groups, which may be bonded to R, the aryl (Ar) group, or the fluorescent (Fl) group.

The water solubilizing groups will for the most part be sulfate, sulfonate, sulfinate, amines amidates, ammonium, phosphate, phosphonate, borate, boronate, carboxamide, carboxylate, hydroxyalkyl groups e.g. saccharides, etc. The water solubilizing group may be directly bonded to an annular carbon atom or may be joined by a linking group, generally a linking group of from about 1 to 4 atoms, usually carbon atoms, normally aliphatic. Alternatively, the water solubilizing group may be bonded to a heteroatom functionality available on an aromatic ring, which may include the heteroatom involved with the activation of the aryl ring or with the fluorescent properties of the fluorogenic group.

For the most part, the precursor compositions of this invention will have the following formula:

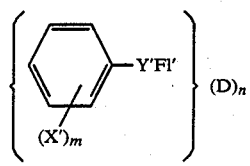

wherein:

X' is oxy or amino, including substituted oxy or amino, where the oxy or amino may be unsubstituted or have some or all of the hydrogen atoms substituted with groups of from 1 to 4, usually from 1 to 3 carbon atoms, normally aliphatic groups free of aliphatic unsaturation and having from 0 to 1 substituent per group, usually water solubilizing substituents, comprising the groups described above, as well as hydroxyl and amino; wherein heteroatoms bonded to saturated aliphatic carbon atoms are separated by at least two carbon atoms;

n is 0 to 6;

D is alkyl of from 1 to 3 carbon atoms, a polar group having from 0 to 6 carbon atoms and 1 to 6 heteroatoms which are oxygen, nitrogen, sulfur and phosphorus, or polyols, including monomeric (5–6 carbon atoms) and polymeric polyols, such as mono- and polysaccharides, and is bound to Ar, Fl or R, particularly to provide water solubility;

at least one of the X's is separated from Y' by either two or four carbon atoms (either ortho or para substitution);

Y' is the same as Y, m is 1 to 2;

the group designated Fl' is a group having a benzene ring bonded to Y' at an annular carbon atom and when taken together with the heteroatom of Y' forms a fluoroscent compound, which is much less fluoroscent at the excitation wavelength of Fl'—Y' when bound to the benzene ring. Thus the fluorescent compound has a capped phenolic or anilino group. Any of the available carbon atoms on the rings may be substituted with a substituent, which includes halides and the substitutents described above, as well as alkyl and alkoxy groups, generally from 1 to 6, more usually from about 1 to 3 carbon atoms, which alkyl and alkoxy groups may be substituted with any of the previously indicated substituents, particularly the water solubilizing functionalities.

Compounds which may be used for the fluorogenic compound include amino- or hydroxyl-substituted derivatives of chromen, xanthen, or the like. Of particular interest are the compounds of coumarin and xanthene.

For the most part, the compounds of this invention having a coumarin group will have the following formula:

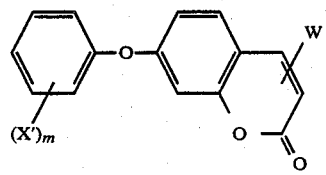

wherein:

X' has been defined previously and any of the annular carbon atoms, as well as X', where X' is hydroxyl and amino, may be substituted by any of the substituent groups described previously, with the understanding that, as appropriate, the heteroatoms will be spaced apart to provide for a stable compound, and that the substituent will not prevent the precursor compound from being a peroxidase substrate. That is, where a heteroatom is bonded to a saturated carbon atom, that same carbon atom will not be bonded to X';

W is hydrogen, lower alkyl (1–3 carbon atoms) carboxy, carboxamide or N-substituted carboxamide;

m is 1 to 2.

It is understood that the substrate may be modified as described previously to enhance water solubility.

A second group of compounds is based on the xanthenes, and include the fluoresceins which will for the most part have the following formula:

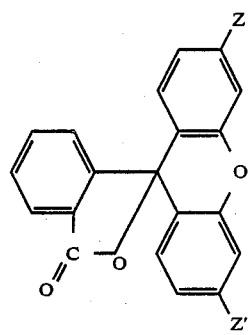

wherein:

Z is of the formula:

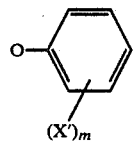

wherein:

X' has been defined previously, at least one of which is separated by 2 or 4 carbon atoms from the oxygen;

m has been defined previously;

Z' is the same as Z or oxy, e.g. hydroxy or lower alkoxy; and wherein any of the annular carbon atoms may be substituted by any of the substituents described previously.

Generally, the activated aryl group will have 0 to 3, usually 0 to 2 substituents bonded to an annular carbon atom or to X, replacing a hydrogen of X, in order to enhance water solubility, modify the chemical properties of the group in acting as a substrate, or the like. Groups of interest include lower alkyl groups of from 1 to 3, usually 1 to 2 carbon atoms, e.g., methyl and ethyl; carboxyalkyl of from 2 to 4, usually 2 to 3 carbon atoms, e.g., carboxymethyl and carboxyethyl; hydroxy- or aminoalkyl of from 1 to 3, usually 1 to 2 carbon atoms, e.g., hydroxymethyl, aminoethyl, and aminomethyl; or alkylsulfonic acid.

The groups on the fluorogenic portion of the molecule may be varied more widely to modify water solubility, the fluorogenic properties of the fluorogenic compound, and the like. A number of illustrative fluorescein derivatives may be found in U.S. Pat. No. 4,318,846 and application Ser. No. 73,158 filed Sept. 7, 1979, entitled, "Novel Alkyl Substituted Fluorescent Compounds and Conjugates," the disclosure of which is incorporated herein by reference.

For the most part these compounds have from 2 to 6, usually 2 to 4 substituents, which include lower alkyl of from 1 to 3, usually 1 to 2 carbon atoms, alkoxy of from 1 to 3, usually 1 to 2 carbon atoms, carboxy and halo, particularly of atomic number 9 to 17, wherein the alkyl group may also be substituted by carboxy.

The carboxy group may be used as a site for further modification, particularly for adding additional functionalities to impart water solubility. Thus, esters and amides may be prepared having alkyl groups substituted with carboxy, sulfur or phosphorus acid groups and of from about 1 to 4, usually 1 to 3 carbon atoms, with the carboxy having 2 to 4, usually 2 to 3 carbon atoms.

Aryl groups which may be used to cap the phenolic group may be illustrated by the following groups:

p-aminophenyl; o-aminophenyl; p-toluidinyl; o-toluidinyl; 4-amino-3,5-dimethylphenyl-1; 4-amino-2-carboxyphenyl-1; 4-amino-2-(2'-carboxymethyl)-1-phenyl; 2,4-dimethoxyphenyl-1; 3,4-diaminophenyl-1; 3-methoxy-4-aminophenyl-1; 4-amino-3,5-dimethoxyphenyl-1; 4-amino-7-carboxynaphthyl-1; p-hydroxyphenyl; 3,5-diethyl-4-hydroxyphenyl-1; 3-carboxymethoxy-4-hydroxyphenyl-1; 4-hydroxyanilino; 2-hydroxy-5-(2'-dimethylaminoethyl)phenyl-1; 4-hydroxy-3-(2-sulfonatoethoxy)-phenyl-1, and 2-hydroxy-4-phosphatomethylphenyl-1.

For the fluorescent compounds, a wide variety of 2-oxo-7-hydroxy and 7-amino coumarins may be employed having a variety of substituents. The following are illustrative coumarin groups which may be joined to the aryl group at the phenolic hydroxyl group:

3-carboxy-2-oxo-7-chromenyloxy; 3-(2'-phosphonatoethyl)-2-oxo-7-chromenyloxy; N-carboxymethyl 3-carboxamide-2-oxo-7-chromenyloxy; N-phosphonatomethyl 3-carboxamide-2-oxo-7-chromenyloxy; 5-(2'-aminoethyl)-2-oxo-7-chromenyloxy; and 5-carboxymethoxymethyl-2-oxo-7-chromenyloxy, N-(2-ethylsulfonic acid)-2-oxo-7-chromenylamino.

Illustrative umbelliferone compounds may be found in U.S. Pat. No. 4,230,797.

The compounds of the subject invention can be made by capping anilino or phenolic fluorescent compounds in accordance with conventional ways. Particularly, ortho- or para-nitroaryl halides may be employed with the fluorescent phenoxide, where the halogen is displaced to form the ether linkage. The nitro group may then be reduced to an amino group in accordance with conventional ways. If desired, the amino group may then be substituted. For hydroxyaryl compounds various reactions can be employed for coupling to the phenolic fluorescer, such as condensation with γ halocyclohexenones followed by dehydrogenation or by employing a benzyne intermediate; carbamyl groups can be obtained using isocyanates with the phenolic group, or the like. The manner in which the subject compounds are made is not critical to the subject invention.

As already indicated, the subject compounds find use in assaying for peroxides, for peroxidase, and more particularly in diagnostic assays employing peroxidase as a label. A large number of patents exist describing the use of enzymes for diagnostic purposes, many of which specifically describe the use of peroxidase as a label. Illustrative patents include 3,654,090, 3,817,837, 4,233,402, 4,275,149 and 4,299,916, which are merely illustrative of the extensive patent literature.

Of particular interest are assays in which the peroxidase enzyme is conjugated with a member of a specific binding pair, which member is either a receptor or a ligand. Ligands can be any analyte of interest for which a receptor exists, while receptors will usually be antibodies or naturally occurring compounds with high specificity for a particular ligand. The conjugate can be used in a variety of ways, particularly where it becomes bound to a surface in proportion to the amount of analyte in the assay medium. Depending upon the particular protocol, after the peroxidase becomes bound, it may be removed from the sample and placed in a separate solution, referred to as a developer solution, containing the fluorogenic precursor substrate according to this invention.

Alternatively, where one has in situ formation of hydrogen peroxide, one can combine the peroxidase conjugate with the fluorogenic precursor as a composition which can be used as a reagent, so that the precursor is oxidized to the stable fluorescer in the presence of the sample. For the purposes of diagnostic assays, the fluorogenic precursors of this invention may be provided as an individual reagent or in combination with other members of the assay system, particularly the peroxidase conjugate.

Exemplary of the use of the subject compositions is employment of a bibulous support to which an oxidase is bound, such as glucose oxidase, which provides a source of hydrogen peroxide at the surface of the support when glucose is provided. To the bibulous support is also bound either ligand or receptor, which is normally homologous to the analyte. The assay is carried out by contacting the bibulous support with an assay medium which contains the sample, the peroxidase conjugate and the fluorogenic precursor according to this invention. The fluorescent product is produced at the surface of the bibulous support and binds to the support, so that the fluorescence from the support may be determined as indicative of the presence and amount of the analyte. One embodiment of this invention may be found in U.S. Pat. No. 4,299,916.

An alternative embodiment involves an immunochromatograph, which is exemplified in U.S. Pat. No.

4,168,146. In this instance, the immunochromatograph would be a combination of a member of a specific binding pair and a source of hydrogen peroxide, such as glucose oxidase. After chromatographing the analyte, the immunochromatograph is contacted with a solution containing the peroxidase conjugate, the fluorogenic precursor according to this invention, and glucose, as well as ancillary reagents, such as buffers, stabilizers, or the like, so that the presence or absence of the analyte would be observable by the production of a fluorogenic signal where the peroxidase conjugate binds.

The following examples are offered by way of illustration and not by way of limitation.

EXPERIMENTAL

Example I

Preparation of 3-carboxy-7-(4'-aminophenoxy)coumarin

Into a reaction flask was introduced 10.68 g (45.6 mmole) of 3-carboethoxyumbelliferone in 300 ml toluene and the mixture heated at reflux for one hour, with 30 ml of distillate removed azeotropically, followed by cooling. To the cooled mixture was then added 1.92 g of sodium hydride and the mixture heated at refluxing for 0.5 hr, while removing the solvent with a Dean-Stark separator. The residue was dried in vacuo overnight.

To about 5 g of the above product suspended in approximately 150 ml DMF was added 3.8 g anhydrous potassium carbonate. The mixture was heated while slowly adding 2.72 g of p-fluoronitrobenzene in about 30 ml DMF. After heating at near refluxing for 2 hours, the reaction was checked by tlc showing incomplete reaction. An additional 1.76 g of the p-fluoronitrobenzene was then added in 20 ml DMF and the reaction allowed to proceed overnight.

After cooling, the mixture was poured onto ice and the precipitate collected by filtration, followed by extraction with $CH_2Cl_2$. Work up yielded 5.3 g of a yellow solid. The major portion of the solid was purified by chromotagraphy on a 4.2 cm $\times$ 34 cm (200 g silica gel 60-200 mesh) column, prepared using $CH_2Cl_2$ as solvent. Approximately 3.5 g of crude material was applied onto the column as a $CH_2Cl_2$ solution, followed by the addition of 100ml $CH_2Cl_2$, followed by elution with 5% of ethyl acetate in $CH_2Cl_2$. While initially 50 ml fractions were collected, this was followed by collecting 15 ml fractions and the fractions containing the desired product were identified by tlc. Fractions were pooled to give about 1.25 g of carboethoxy-7-(4'-nitrophenoxy)coumarin, m.p. 163° C.

Into 3 ml of 50% aqueous ethanol was added 38 mg of the above product and 52 mg of ferrous chloride. The mixture was stirred rapidly with gradual heating while a solution of 5 $\mu l$ of conc. HCl in 1 ml 50% aqueous ethanol was added slowly. The mixture was then refluxed for 2 hours. After cooling, the reaction mixture was diluted with a few ml of water and extracted with ether. The combined ether extracts were dried over anhydrous sodium sulfate, the solvent evaporated, yielding 18 mg of 3-carboethoxy-7-(4'-aminophenoxy)-coumarin. m.p. 136°-138° C. NMR and tlc were consistent with the desired product.

The above amino ester was dissolved in dioxane and an equal volume of cold 20% sulfuric acid added. The mixture was then heated at reflux overnight. After cooling, the pH was adjusted to pH 5 with aqueous sodium hydroxide, whereby a precipitate formed which was collected by filtration. The precipitate was dissolved in a large volume of boiling water, quickly filtered while hot, and upon cooling the title compound precipitated out. m.p. 213°-214° C. (dec.)

Enhanced yields could be obtained by extracting the neutralized medium with ethyl acetate or diethyl ether, and purifying the resulting extracts.

Example II.

Preparation of 3-carboxy-7-(3'-methyl-4'-aminophenoxy)coumarin

Into about 10 ml dry DMF was suspended 330 mg of the sodium salt of 3-carbethoxyumbelliferone and the mixture heated to about 130° C., where upon most of the salt dissolved. Approximately 300-400 $\mu l$ of 3-methyl-4-nitrofluorobenzene was added slowly dropwise (2-3min/drop), while maintaining a nitrogen atmosphere and slowly raising the temperature to about 170° C. over a 5 hour period. The reaction was then terminated, the solution cooled and ice water added, followed by extraction with diethyl ether. The combined ether extracts were washed twice with sat. sodium bicarbonate, brine, followed by drying over anhydrous sodium sulfate. The solvent was removed by evaporation leaving a solid yellow material, which was purified by preparative tlc to yield approximately 140 mg of a pure nearly white compound. m.p. 158° C.

Into 25 ml of 50% aqueous ethanol was suspended 155 mg of the above product, followed by the addition of 180 mg of ferrous chloride and 15 $\mu l$ of conc. HCl which was diluted with aqueous ethanol before addition. The mixture was heated to reflux for 3 hours, followed by filtration and extraction with $CH_2Cl_2$. The extracts were washed, dried, and evaporated to dryness and the product purified with preparative tlc. The aromatic amino compound appeared to degrade during the purification.

Into a 1:1 mixture of 12 ml of 20% (v/v) of aqueous sulfuric acid and dioxane was suspended 50 mg of the above product and the mixture heated to reflux overnight. After cooling, the solution was neutralized with 1N sodium hydroxide to pH ca.5. A precipitate formed which was collected by filtration and resuspended in about 80 ml water. The mixture was heated to boiling, filtered while hot, the filtrate allowed to cool and the precipitated product isolated by filtration yielding about 18 mg after drying. Tlc indicated the possibility of a trace amount of 3-carboxyumbelliferone contaminant. m.p. 204°-206° C. (dec.)

Example III

Preparation of 3-carboxy-7-(N-carboxymethyl 4'-aminophenoxy)coumarin

Into about 5 ml of dry DMF was dissolved 218 mg (0.67 mmole) of the 3-carboethoxy-7-(4'-aminophenoxy)coumarin under a nitrogen atmosphere. After adding a small amount of anhydrous sodium carbonate, 421 mg of ethyl iodoacetate was added very slowly dropwise at room temperature, followed by stirring the mixture at room temperature for several hours. Tlc showed only a small amount of product, so the reaction mix was heated to about 40° C. for one hour and then allowed to cool to room temperature and stirring continued for 2 days. The reaction was worked up by pouring the mixture onto water and extracting with $CH_2Cl_2$. The combined $CH_2Cl_2$ extracts were washed with sat. aqueous sodium bicarbonate, brine, and then dried over anhydrous sodium sulfate. By removal of the solvent, an orange solid residue was obtained weighing approximately 250 mg. m.p. 118°–119° C.

Into 5 ml dioxane was dissolved 218 mg of the above product followed by the addition of an equal volume cold 10% (v/v) aqueous sulfuric acid. After heating at reflux for 5 hr, the reaction mixture was worked up by extraction with ether and some difficulties encountered in obtaining a sharp interface. The combined ether extracts were partitioned with sat. aqueous sodium bicarbonate. The aqueous layer was separated and acidified with 4N HCl, followed by extraction with ether. The combined ether extracts were dried over anh. magnesium sulfate, and the solvent removed in vacuo, providing a yellow solid. m.p. 165° C. (dec.; turning orange-red at 150° C.). The product was found to be useful as an HRP substrate.

Example IV

Preparation of taurine derivative of 3-carboxy-7-(3′-methyl-4′-aminophenoxy)coumarin In about 1.5 ml of dry DMF was mixed 102 mg (0.33 mmole) of the product of Example II, 38 mg (0.33 mmole) of N-hydroxy succinimide and 78 mg of dicyclohexylcarbodiimide and the mixture stirred under nitrogen for about hours and then filtered through glass wool.

Taurine (80 mg) was dissolved in 1 ml distilled water, and the pH adjusted to about 7.5 with 0.1N NaOH. The solution was then added gradually to the above mixture. Cloudiness and some precipitate was substantially removed by the addition of DMF. The mixture was immersed in a hot water bath (about 50° C.) and stirred overnight, while the temperature dropped to room temperature.

The precipitate was separated by filtration through a glass wool plug, the filtrate evaporated to dryness, the residue resuspended in DMF and the solution filtered, and the filtered solution re-evaporated to dryness to leave a brown residue. Preparative liquid chromotography was employed with methanol: methylene chloride: water (10:60:1) and the product added in a solution of DMF and water. The yellow band near the baseline was scraped off and eluted using DMF. The product was dried. A large fluorescent background indicated the presence of a fluorescent contaminant, so that the product was further purified employing a Sephadex G-10 Column (1.1×11 cm) and a solution of 5 mg of the product in 0.5 ml of water added to the column and the product eluted with water. Fractions (1 ml) were collected and their fluorescent spectra determined. Fractions having low fluorescence were collected and pooled. The procedure was repeated in order to reduce the background fluorescence.

The product was shown to be useful as a HRP substrate by combining the above compound with HRP and $H_2O_2$ in an aqueous solution and observing the generation of a fluorescent product.

Example V

Preparation of glucosamine derivative of 3-carboxy-7-(3′-methyl-4′aminophenoxy)coumarin The N-hydroxy succinimide ester was prepared as described in Example IV. 2-Amino-2-deoxyglucose hydrochloride (39 mg, 0.181 mmole) was dissolved in a small amount of water and the pH brought to 7.5–7.6 with 0.1N sodium hydroxide. Under a nitrogen atmosphere, a DMF solution of the above ester (51.9 mg of the acid, 0.167 mmole) was added with stirring and the stirring continued overnight. Purification was carried out using preparative liquid chromotography (PLKC 18F linear K reverse phase plates) using the previously described solvent system. The middle Rf component was scraped off and eluted with methanol, a small amount of the binder being incorporated.

The sample was filtered through a sintered glass filter to obtain a clear solution, the solvent evaporated and the residue dissolved in 5 ml DMF. The solution was then evaporated to dryness, dissolved in 1 ml. DMF, followed by a dilution with 4 ml buffer and an assay carried out as described previously employing 100 microliters of the substrate. The product was found to be active as an HRP substrate.

Example VI.

Preparation of 3-carboxy-7-(3′-methyl-4′-amino-5′-bromophenoxy)-coumarin

Into a flask was introduced 59 mg (0.174 mmole) of the ethyl ester of 3-carboxy-7-(3′-methyl-4′-aminophenoxy)coumarin (see Example II), 34 mg (0.19 mmole) of N-bromo succinimide and 1.45 ml dry DMF, the flask sealed with a septum and a stream of nitrogen maintained. The solution turned dark purple, and the mixture was allowed to stir overnight at room temperature. After pouring the reaction mixture onto ice-water, the solution was extracted with $CH_2Cl_2$ and the combined extracts washed with sat. sodium bicarbonate, brine, and then dried over anhydrous sodium sulfate. The solvent was removed and the residue purified employing tlc.

The brominated product (10–15 mg) was dissolved in about 1 ml dioxane and 0.5 ml 20% sulfuric acid added, and the mixture heated and refluxed overnight. After cooling, the solution was neutralized with 1N sodium hydroxide until a precipitate formed, the precipitate allowed to settle and the mixture filtered. The solid precipitate was suspended in hot water which was heated to boiling and then filtered. The filtrate was allowed to cool and then concentrated in vacuo to about 40 ml, and the precipitate collected by filtration. After redissolving in DMF and filtering, the resulting yellow solution was evaporated leaving about 10–11 mg of the product. By employing an assay as described previously, the product was shown to be an active HRP substrate.

Example VII

Preparation of Horseradish Peroxidaseanti(polyribosephosphate) antibody (HRP-antiPRP) conjugate To HRP (Sigma, 150 mg) in 20 ml distilled water was added 4 ml 0.1M $NaIO_4$, the mixture stirred for 20 min at room temperature, followed by the addition of 2.4 ml 1M glycerol. After stirring at room temperature for 30 min, the reaction mixture was dialysed 3×500 ml 2 mM sodium acetate, pH 4.5.

The antiPRP solution (*Hemophilus influenzae*; available from the Division of Laboratories and Research, Department of Health, New York State, M-3 lot 28A) was diluted to 9 ml and dialysed 3×500 ml, 10 mM $Na_2CO_3$, pH9.5. After dialysis 1:50 dilution gave an $OD_{280}=0.656$ (~23.43 mg/ml).

To 21.64 ml (67.73 mg) of the activated HRP was added 4.67 ml (109.4 mg) of antiPRP, the mixture diluted to 29.9 ml with 10 mM $Na_2CO_3$, pH9.6 and the pH adjusted to 9.6 using 0.1N NaOH. After stirring for 2 hrs. at room temperature, the mixture was cooled in an ice bath and 1.5 ml (4 mg/ml) $NaBH_4$ added, while protecting the reaction mixture from light and stirring for 2 hrs at 0° C. The mixture was then dialysed overnight against 1 liter PBS buffer (10 mM $PO_4$, 0.15M NaCl, pH 7.2).

The conjugate was then chromatographed using a collodion apparatus on a Biogel ASM column (2.5×90 cm), collecting 5 ml fractions and eluting with PBS containing 0.01%$NaN_3$. Fractions 39–48 were pooled; $A_{280}=0.619$; $A_{403}=0.332$.

To demonstrate the utility of the fluorogenic precursors of the subject invention, the following exemplary assay was carried out. Microtiter plate wells were coated with a solution (250 μl/well) of an amine modified glucose oxidase (1 to 190 dilution, 7.6 mg/ml stock solution) and antibodies to polyribosephosphate (1:2000 dilution in 60 mM carbonate buffer, pH 9.6). After standing overnight, the wells were washed with PBS containing 0.05% Tween 20 (W/V).

A stock solution was prepared of the fluorogenic substrate of Example II. A 3.8 mg/10 ml DMF solution (1.22 mM) was diluted 1:10 with PBS buffer immediately before use. A substrate mixture was prepared containing 500 μl of the above stock solution, 694 μl of 1.8M glucose, 400 μl of a stock catalase solution and the volume brought to 2 ml with PBS buffer. The stock catalase solution (3.1–4 mg/ml) was prepared by dialysing catalase (C-100 Sigma) in PBS pH 7.2.

The following protocol was then employed for the assay. Into each microtiter well coated with amino glucose oxidase (see copending application serial No. 398,505, filed July 15, 1982) and antiPRP was added 100 μl of 50 ng/ml PRP or 100 μl of PBS buffer (pH 7.2) and the mixture incubated for one hour at room temperature. At the end of this time, 50 μl of HRP-antiPRP conjugate was added followed by another one hour incubation. At the end of this time, 100 μl of a substrate mixture was added, followed by a 10 minute incubation at 37° C. with shaking, after which time 200 μl of the incubation mixture was diluted with 1.8 ml, of 0.1M phosphate buffer (pH 8.0) and the fluorescence read.

The following table indicates the results with varying concentrations of the HRP-antiPRP conjugate, in the presence and absence of PRP.

TABLE I

| Dilution of HRP-antiPRP | Fluorescence | |
|---|---|---|
| | with PRP | without PRP |
| 1:80 | 79.5 | 67.1 |
| 1:320 | 31.8 | 11.0 |
| 1:320 | 29.6 | 14.2 |
| 1:320 | 32.5 | 13.4 |
| 1:1280 | 13.8 | 5.2 |
| 0 | 2.2 | 2.4 |

In the next assay, the fluorogenic precursor of Example I was employed. The test was to demonstrate that the compound of Example I is a substrate for HRP. An assay solution was prepared comprising the chromogenic compound of Example I, hydrogen peroxide, horse radish peroxidase, and buffer (0.1M phosphate, pH 8.0) and the change in fluorescence in the solution determined over a 60 second interval. The substrate solution which was added was 3.9 mg/100 ml concentration in buffer, the hydrogen peroxide was $9.\times10^{-4}M$, the HRP solution was 6.6 ng/ml containing 0.5 mgBSA/ml and the buffer was 0.1M phosphate, pH 8. The following table indicates the results.

TABLE II

| Substrate μl | $H_2O_2$ μl | HRP μl | Buffer μl | ΔF |
|---|---|---|---|---|
| 800 | 100 | 0 | 100 | 6.6 |
| 800 | 100 | 20 | 80 | 11.0 |
| 800 | 100 | 50 | 50 | 16.2 |
| 800 | 100 | 100 | 0 | 29.7 |
| 800 | 100 | 100 | 0 | 30.4 |

It is evident from the above results, that the subject compositions are efficient substrates for HRP. The fluorogenic precursor is rapidly converted to a fluorescent product. The product resulting from the aryl cap does not interfere with the fluorescence of the fluorescent product, nor does it inhibit the enzyme reaction. Furthermore, at appropriate basic pH at which horseradish peroxidase has high catalytic activity, the fluorescent product is stable and has a high quantum efficiency. Thus, the subject fluorogenic substrates provide a convenient and simple way for performing fluorescent assays for a wide variety of analytes of interest either in a heterogeneous or homogeneous mode.

Although the foregoing invention has been described in some detail by way of illustration and example for purposes of clarity of understanding, it will be obvious that certain changes and modifications may be practiced within the scope of the appended claims.

What is claimed is:

1. In a method for determining the catalytic activity of a perioxidase by measuring the amount of a product produced from a subtrate of said peroxidase, which product provides a fluorometric signal, the improvement which comprises employing as fluorogenic substrate a diaryl organic compound consisting of an aryl fluorescent compound linked by means of a linking group to a carbocyclic aryl group wherein said linking group has a nitrogen or oxygen bonded to a ring carbon atom of said aryl fluorescent compound and an oxygen bonded to a ring carbon atom of said carbocylic aryl group, which diaryl organic compound is non-fluorescent at the excitation wavelength of said aryl fluorescent compound when said aryl fluorescent compound is linked to said carbocylic aryl group, said carbocylic aryl group having an oxy or amino substituent on a ring carbon atom separated by 2 or 4 ring carbon atoms from the ring carbon atom attached to said linking group, which carbocyclic aryl group undergoes perioxidase catalyzed removal as a result of cleavage of said linking group to produce said aryl fluorescent compound.

2. A method according to claim 1, wherein said carbocyclic aryl group is an hydroxyphenyl.

3. A method according to claim 1, wherein carbocyclic aryl group is an aminophenyl.

4. A method according to any of claims 2 or 3, wherein said group is para.

5. A method according to claim 1, wherein said carbocyclic aryl group is an oxyaryl group.

6. A method according to claim 1, wherein said carbocyclic aryl group is an aminoaryl group.

7. A method according to claim 1, wherein said carbocyclic aryl group is phenyl.

8. In a method for determining the presence of an analyte in a sanple employing in said method periodidase as a label, wherein said peroxidase is conjugated to a member of a specific binding pair, said pair consisting of ligand and receptor, and said analyte is a member of said pair, said method comprising combining said conjugate, said sample, a source of peroxide, and a substrate for perioxidase, which substrate results in a product producing a detectable signal; and determining the amount of product produced, which amount is related to the amount of analyte in said sample, the improvement which comprises employing as a fluorogenic substrate a diaryl organic compound consisting of an aryl fluorescent compound linked by means of a linking group to a carbocyclic aryl group wherein said linking group has a nitrogen or oxygen bonded to a ring carbon atom of said aryl fluorescent compound and an oxygen bonded to a ring carbon atom of said carbocyclic aryl group, which diaryl organic compound is non-fluorescent at the excitation wavelength of said aryl fluorescent compound when said aryl fluorescent compound is linked to said carbocylic aryl group, said carbocylic aryl group having an oxy or amino substituent on a ring carbon atom separated by 2 or 4 ring carbon atoms from the ring carbon atom attached to said linking group, which carbocylic aryl group undergoes peroxidase catalyzed removal as a result of cleavage of said linking group to produce said aryl fluorescent compound.

9. A method according to claim 8, wherein said source of peroxide is the combination of an oxidase and substrate for said oxidase.

10. A method according to claim 8, wherein said carbocyclic aryl group is an oxyaryl group.

11. A method according to claim 8, wherein said carboxyclic aryl group is an aminoaryl group.

12. A method according to claim 8, wherein said carbocyclic aryl group is phenyl.

* * * * *